United States Patent
Guo et al.

(10) Patent No.: US 11,189,380 B2
(45) Date of Patent: Nov. 30, 2021

(54) OUTCOME-DRIVEN TRAJECTORY TRACKING

(71) Applicant: International Business Machines Corporation, Armonk, NY (US)

(72) Inventors: Shi Jing Guo, Beijing (CN); Xiang Li, Beijing (CN); Hai Feng Liu, Beijing (CN); Shi Wan Zhao, Beijing (CN); Zhi Qiao, Beijing (CN); Guo Tong Xie, Beijing (CN)

(73) Assignee: International Business Machines Corporation, Armonk, NY (US)

( * ) Notice: Subject to any disclaimer, the term of this patent is extended or adjusted under 35 U.S.C. 154(b) by 1037 days.

(21) Appl. No.: 15/825,156

(22) Filed: Nov. 29, 2017

(65) Prior Publication Data
US 2019/0163874 A1 May 30, 2019

(51) Int. Cl.
| | | |
|---|---|---|
| *G06F 3/048* | (2013.01) | |
| *G16H 50/50* | (2018.01) | |
| *G16H 15/00* | (2018.01) | |
| *G16H 50/20* | (2018.01) | |
| *G16H 20/10* | (2018.01) | |

(Continued)

(52) U.S. Cl.
CPC .......... *G16H 50/50* (2018.01); *G16H 15/00* (2018.01); *G16H 20/10* (2018.01); *G16H 50/20* (2018.01); *G16H 50/30* (2018.01); *G05B 13/048* (2013.01)

(58) Field of Classification Search
None
See application file for complete search history.

(56) References Cited

U.S. PATENT DOCUMENTS

| | | | |
|---|---|---|---|
| 2015/0112710 A1 | 4/2015 | Haber et al. | |
| 2021/0142915 A1* | 5/2021 | Haber | G16H 50/30 |

FOREIGN PATENT DOCUMENTS

| | | |
|---|---|---|
| WO | 2014145705 A2 | 9/2014 |
| WO | 2016036831 A1 | 3/2016 |
| WO | 2017029314 A1 | 2/2017 |

OTHER PUBLICATIONS

Nagin et al., "Group-Based Trajectory Modeling in Clinical Research", Annu. Rev. Clin. Psychol., Jan. 4, 2010, DOI: 10.1146/annurev.clinpsy.121208.131413, Copyright 2010 by Annual Reviews, 32 pages.

(Continued)

*Primary Examiner* — William C Trapanese
(74) *Attorney, Agent, or Firm* — Stosch Sabo

(57) ABSTRACT

A dataset regarding a plurality of applications is obtained. A set of parameters is determined from the dataset, comprising at least a sample performance trajectory, a risk factor, and a performance outcome. A maximum likelihood of each performance outcome is determined using a likelihood function, the likelihood function being a mixture model of a trajectory model and an outcome model. The set of parameters is updated according to the maximum likelihood of each performance outcome. A performance trajectory model is built according to the updated set of parameters. The plurality of applications is then grouped into subgroups according to the performance trajectory model, each subgroup containing one or more applications, and each of the one or more applications in a given subgroup having a same or similar trajectory to each other. An alert associated with the applications in at least one of subgroups may be generated.

12 Claims, 5 Drawing Sheets

(51) Int. Cl.
*G16H 50/30* (2018.01)
*G05B 13/04* (2006.01)

(56) References Cited

OTHER PUBLICATIONS

Franklin et al., "Group-based Trajectory Models: A New Approach to Classifying and Predicting Long-Term Medication Adherence", Medical Care, May 2013, DOI: 10.1097/MLR.0b013e3182984c1f, 9 pages.

* cited by examiner

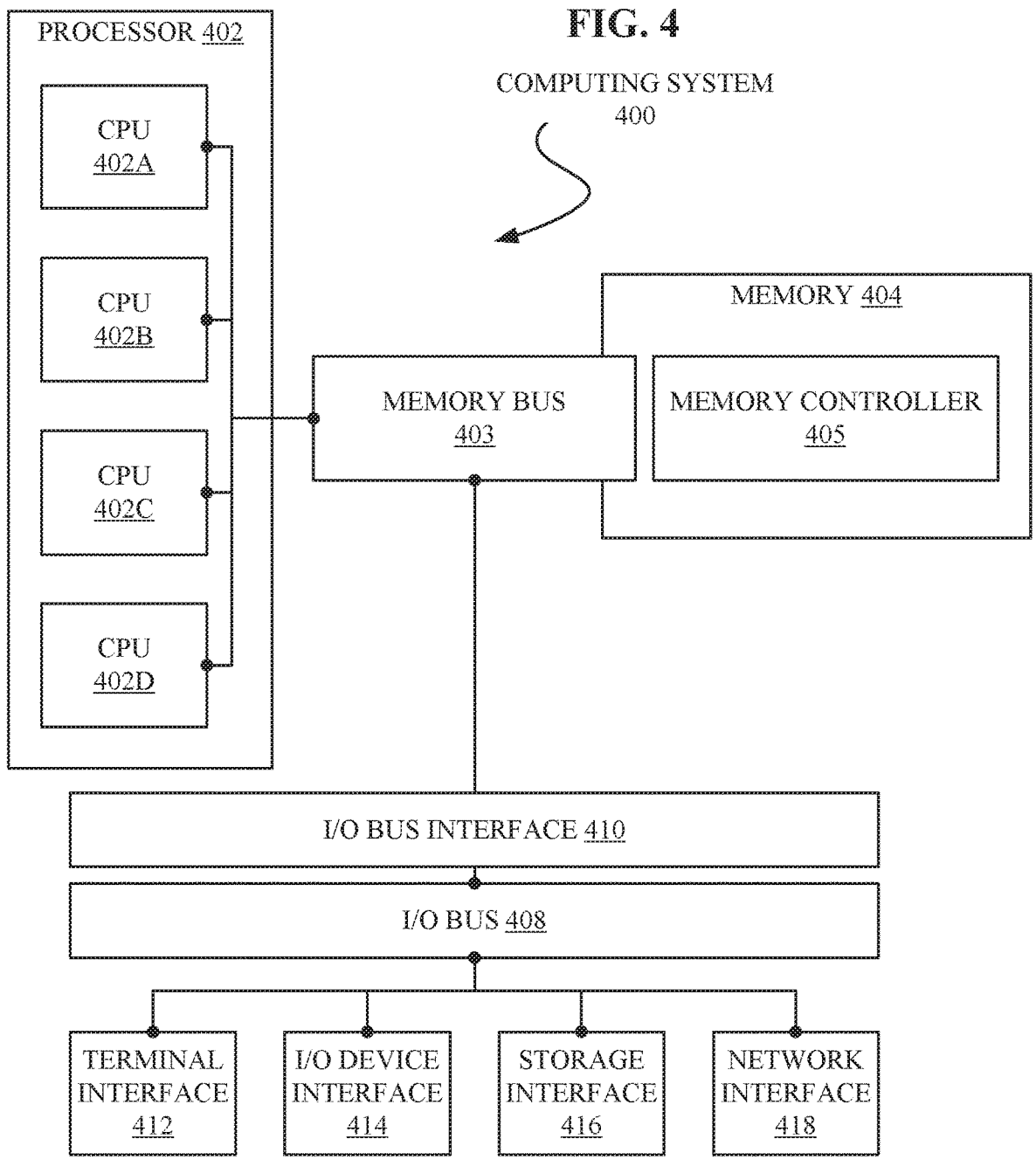

OUTCOME-DRIVEN TRAJECTORY TRACKING

BACKGROUND

The present disclosure relates to applying trajectory grouping, and more specifically, to generating outcome alerts by tracking and applying trajectory grouping.

In determining a pattern of activity (e.g., finding a pattern in an application's performance, such as for application performance management) a longitudinal sequence of measurements may be used to determine a trajectory of the activity. For example, an application's response time may be measured every day over a period of time to determine a trajectory for that application's response time. When applications with similar trajectories are grouped together accordingly, it is referred to as a group-based trajectory.

SUMMARY

According to embodiments of the present disclosure, a method of generating alerts by tracking an outcome-driven trajectory is described. A dataset associated with computing performance of a plurality of applications is obtained. From the dataset, a set of parameters is determined, comprising at least a sample performance trajectory for each of the plurality of applications, a risk factor associated with one or more of the plurality of applications, and a performance outcome projected for each of the plurality of applications according to each application's sample performance trajectory. A maximum likelihood of each performance outcome is determined using a likelihood function, the likelihood function being a mixture model of a trajectory model and an outcome model. The set of parameters is updated according to the maximum likelihood of each performance outcome. A performance trajectory model is built, using the dataset, according to the updated set of parameters. The plurality of applications is then grouped into subgroups according to the performance trajectory model, each subgroup containing one or more applications, and each of the one or more applications in a given subgroup having a same or similar trajectory to each other. An alert associated with the applications in at least one of subgroups may be generated.

In another embodiment, a dataset associated with a plurality of entities is obtained. From the dataset, a set of parameters is determined comprising at least a sample trajectory for each of the plurality of entities, a risk factor associated with one or more of the plurality of entities, and an outcome projected for each of the plurality of entities according to each entity's sample trajectory. A maximum likelihood of each outcome is calculated using a likelihood function, the likelihood function being a mixture model of a trajectory model and an outcome model. The set of parameters is updated according to the maximum likelihood of each outcome. An updated trajectory model is built, using the dataset, according to the updated set of parameters. The plurality of entities is grouped into subgroups according to the updated trajectory model, each subgroup containing one or more entities, and each of the one or more entities in a given subgroup having a same or similar trajectory to each other. An alert associated with the entities in at least one of subgroups may be generated.

A computing system and computer program product can embody the method and structures of the disclosure. The computing system can comprise a network, a memory configured to store a dataset, and a processor in communication with the memory. The computing system can be configured to perform the method.

The above summary is not intended to describe each illustrated embodiment or every implementation of the present disclosure.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

FIG. 4 depicts a high-level block diagram of an example computer system that may be used in implementing one or more of the methods or modules described herein, in accordance with embodiments of the present disclosure.

Figure 1A:
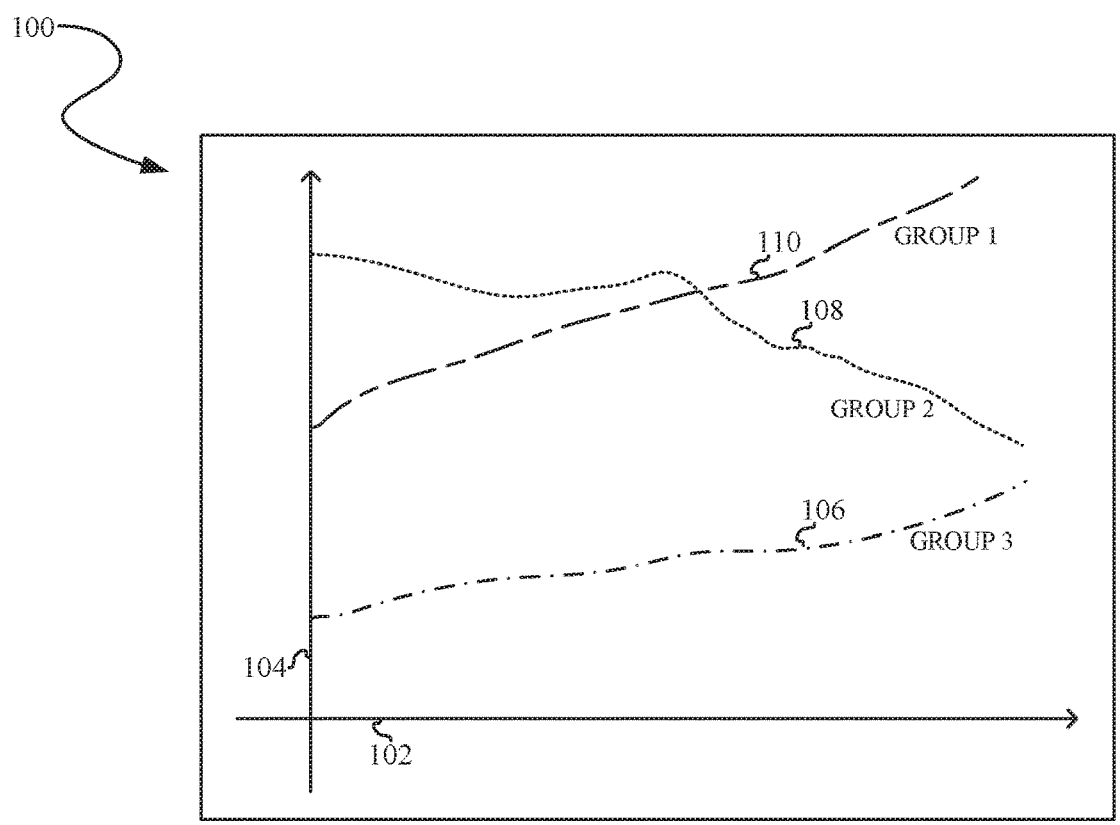
FIG. 1A depicts an example graph of group based trajectories.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

Aspects of the present disclosure relate to trajectory grouping, more particular aspects relate to generating outcome alerts by tracking and applying trajectory grouping. While the present disclosure is not necessarily limited to such applications, various aspects of the disclosure may be appreciated through a discussion of various examples using this context.

Trajectory models may be useful in predicting outcomes. Trajectory data may present patterns that, once identified, may be used to determine possible outcomes to which those trajectories might lead. These patterns may be, for example, patterns in one data value plotted with respect to another data value (e.g., activity plotted with respect to time), the patterns in the derivative of such a plot, etc. The trajectory associated with such patterns may be the path of a curve that connects data values in a data set.

Trajectory models may be useful when categorizing populations of entities or individuals (e.g., persons, machines, computer applications) into groups or subgroups based on trajectory patterns that are shared by some members of the population. For example, a behavior (e.g., an action or pattern of actions by an individual, actions by or performance of a computer system) of a population of entities may be plotted with respect to a variable (e.g., time). The entities in a particular group in the population may exhibit similar trajectory patterns for the behavior, relative to the trajectory patterns exhibited by other entities in the population not in that particular group. In some models, trajectory-based groupings may be useful to identify patterns and resulting outcomes associated with the similar behavior expressed by the similar trajectories. For example, properties (or other, related behaviors) may be shared by individuals in a group but not by individuals in disparate groups. Those properties may then potentially be associated with the trajectory patterns of the behavior or a predicted outcome of the trajectory patterns of the behavior. Further, some trajectory groups may also be useful for recognizing risks that are shared among a given group of individuals. A risk may be, for example, a factor driving a trajectory towards one outcome or another.

For example, a group of computers (e.g., a company's large supply of networked workstations, a set of servers in a server farm) or applications (e.g., a user's personalized collection of applications on his or her mobile device) may be sorted into subgroups based on trajectory patterns derived from their performance data over time. For example, the performance of a group of storage servers may be tested periodically by the owner of the servers (e.g., a data-storage or data-backup service provider) on a variety of tasks (e.g., writing, reading, or transferring test packages of data). The trajectory patterns of the performance of those servers over time may be used to categorize the servers into subgroups based on similar performance trajectories. The trajectories of the subgroups may be correlated with tracked behaviors (e.g., patterns of server usage or maintenance routines) that members of the subgroups tend to share, and over which members of disparate subgroups tend to differ. In such cases, the trajectories of the subgroups may also be correlated with risks associated with the servers (e.g., disc failure and performance slowdowns) in some subgroups, and the trajectories and/or the outcomes of different subgroups may be correlated with different risks.

As another example, patients may be sorted into groups based on having different blood pressure trajectory patterns (e.g., changes in blood pressure measurements over time), with the disparate patient groups having different disease risks according to their different blood pressure trajectories. Further, different subgroups may have different risk prediction models. For example, a model may have two groups: a first group having good medication adherence to an anti-hypertension drug, and a second group having poor medication adherence (e.g., patients may have ceased taking the drug). Between these two groups, a trajectory based on blood pressure may be strongly correlated with disease risks in the second group, those risks may not apply to the first group due to the mitigating effect of the drug.

As discussed, group-based trajectory modeling provides a means of clustering individuals into different subgroups according to their similar trajectories. Further, as the above examples show, accurate grouping of a population of individuals may impact the effectiveness of a trajectory model's risk prediction for a particular group or subgroup. However, traditional group-based trajectory modeling does not consider sample outcomes, and therefore individuals within the same subgroup may fit different outcome prediction models. Thus, the trajectory subgroups make minimal contribution to the outcome prediction using this method. Therefore, in many situations trajectory modeling may be limited in its use to accurately form subgroups of a population. Logistic regression modeling, on the other hand, is a method of predicting a binary outcome risk.

Disclosed herein is a method for developing a trajectory model with consideration to outcome risk by incorporating the outcome-prediction capabilities of logistic regression modeling in group-based trajectory modeling. This may allow for a more accurate predictive model to be separately built for each subgroup in a population of individuals. This may be useful, for example, in more accurately predicting the failure of groups of computer hardware in large populations of computers (e.g., workstations or servers) to help prevent the expenses of unexpected loss of hardware. This may also be useful in more accurately recognizing disease risks among groups of patient populations, or ineffective treatments among a drug regimen.

According to embodiments of the present disclosure, a mixture model, that combines consideration of both of a sample's trajectory and the sample's risk, is applied to calculate a likelihood L for a given sample i:

$$L = \sum_{k=1}^{K} Pr(C_i = k) Pr(Y_i = y_i | C_i = k) Pr(O_i = o_i | C_i = k, X_i = x_i)$$

where C is a group membership (ranged from 1 to k), y is a sequence of longitudinal measurements of a behavior, o is an outcome, and x is a series of risk factors. In this situation, the probability of a given of a given individual's (i) group membership ($C_i$) in a group (ranged from 1 to k) is:

$$[Pr(C_i=k)]=\theta_k$$

For binary data, regarding observation of the measured behavior and group membership, the probability that a given behavior ($y_i$) of a group of behaviors ($Y_i$) would occur given the parameter of the individual's group membership ($C_i=k$) is obtained according to the equation:

$$[Pr(Y_i=y_i|C_i=k)]=\Pi_{y_{ij}=1} P_{ijk} \Pi(1-P_{ijk})$$

where j is a time point at which a value y is observed, with:

$$P_{ijk} = \frac{\exp(\beta_{ok} + t_{ij}\beta_{1k} + t_{ij2}\beta_{2k} + \ldots)}{1 + \exp(\beta_{ok} + t_{ij}\beta_{1k} + t_{ij2}\beta_{2k} + \ldots)}$$

For outcome assessments, the probability of a given outcome ($o_i$) of a group of outcomes ($O_i$) will occur given the parameters of group membership ($C_i=k$) and a given risk factor ($x_i$) of a group of risk factors ($X_i$) is determined according to the following:

$$[Pr(O_i = o_i | C_i = k, X_i = x_i)] = \frac{\exp(\alpha_{ok} + \alpha_{1k}x_1 + \alpha_{2k}x_2 + \ldots)}{1 + \exp(\alpha_{ok} + \alpha_{1k}x_1 + \alpha_{2k}x_2 + \ldots)}$$

Generally, a censored (or regular) normal model may be used for scale data. A zero inflated (or regular) Poisson model may be used for count data. A Bernoulli model (or logistic model) may be used for binary data.

The likelihood function may be examined for a group size $N(\Pi_{i=1}^{N} f(y_i))$, so that the log of the likelihood function is:

$$L=\log(\Sigma_{i=1}^{N} f(y_i))=\Sigma_{i=1}^{N} \log(f(y_i))$$

$$L=\Sigma_{i=1}^{N} \log(\Sigma_{k=1}^{K} Pr(C_i=k)Pr(Y_i=y_i|C_i=k)Pr(O_i=o_i|C_i=k,X_i=x_i)$$

According to embodiments, disclosed herein is a computer system for predicting outcome risk associated with a trajectory. The system includes a memory and a processor in communication with the memory configured to perform a method as described by way of various examples below. A computer may incorporate the memory and the processor, and a plurality of remote devices may be in in communication with the computer via a network. The computer may determine a performance trajectory, incorporating predicted outcomes, of each remote device based in part on grouping the remote devices into subgroups based on similarities in trajectories. Outcome risks associated with those subgroups of computers may be identified. An alert may be generated and selectively transmitted to those remote devices in the subgroup(s) associated with the alert, or to another computing system that manages those remote devices.

In embodiments, the alert may indicate that the one or more remote devices in the associated subgroup exceed a predetermined risk level. The predetermined risk level may be associated with the risk factor from the dataset. For example, a dataset associated with the periodic performance of a process or application running on one or more computers is obtained. For example, the response time, completion time, or the accuracy of the outputs of an activity or activities performed by several deep learning or artificial-intelligence computing systems in a data center may be periodically observed and added to the dataset (as in, computing systems may be the "individuals," and the activities may be the "behaviors"). From the dataset, a set of parameters is determined. The set of parameters comprises a sample performance trajectory for each of the plurality of computing systems, a risk factor associated with one or more of the plurality of computing systems, and a performance outcome projected for each of the plurality of computing systems according to each computing system's sample performance trajectory. Specifically, the set of parameters may comprise a trajectory pattern of each computing system's performance of the activity, or activities, over time. The performance outcome projected may comprise failure of the computing system, failure of a component of the computing system, training of the computing system towards inaccuracy (e.g., in a deep-learning neural network), etc.

Using the set of parameters, a posterior probability for each performance outcome is calculated. A gradient descent is applied to a likelihood function using the posterior probability, and a maximum likelihood for each performance outcome is determined. The likelihood function is a mixture model of a trajectory model and an outcome model. The set of parameters is updated according to the maximum likelihood of each performance outcome. A performance trajectory model is built using the dataset and according to the updated set of parameters. The plurality of computing systems are then arranged into subgroups according to the performance trajectory model. Each subgroup may contain one or more computing systems having a same or similar trajectory to each other (i.e., a same or similar pattern of completion time of an activity, or accuracy of the outputs of that activity).

An alert associated with the computing systems in at least one of the subgroups may then be generated. For example, this method may be utilized in a group of computers performing artificial-intelligence operations. A subgroup of these computers may be associated with a risk of failure of a processing unit (e.g., a graphics processing unit) or a peripheral component (e.g., a cooling fan or pump or power supply) of the members of the subgroup. By accurately grouping these computers, this failure outcome may be more accurately predicted (than by a model not accounting for outcomes) and an appropriate alert issued. In embodiments, this may prevent unexpected failure of components or the associated computers, as other members of the group, having a shared trajectory, may be identified to share the tendency toward the failure outcome. In other embodiments, the increased accuracy of grouping units according to probably outcomes may enable the operators of the artificial-intelligence computers to push the computers closer to the edge of their operating ranges, increasing the processing performance of the individual computers and the data center as a whole. In embodiments, the increased accuracy of grouping and associated behavior prediction may enable the operators of the computers to run components or computers for a longer life cycle before preemptive replacement or maintenance, defraying the associated costs until they are more likely to be needed.

In some embodiments of the disclosure, the alert may trigger an automatic response by a system managing the computers, or by the computers themselves. Using the increased grouping accuracy of the outcome-based trajectory, a subgroup of servers in a storage system may be identified. The subgroup of servers may be identified according to a risk of early failure due to one or more storage drives in those servers having a higher-than average sensitivity to heat (e.g., as a result of unintended manufacturing differences). An alert of this risk may be provided to a manager of the storage system, which may then automatically increase the power delivered to the cooling system of the servers in that subgroup (e.g., to increase fan or pump speeds). While this may result in an inefficient operation of the cooling system if applied throughout the storage system, and may be more expensive due to the increased power requirements, it may be less inefficient and less expensive than one or more of the servers in the subgroup failing prematurely.

In embodiments, the described steps may be performed iteratively until, for example, a difference between a most recent set of parameters and an immediately preceding set of parameters reaches a predetermined threshold. The iterative steps may include calculating a posterior probability according to the dataset, determining a maximum likelihood by applying gradient descent to a likelihood function using the posterior probability, and obtaining updated parameters according to the maximum likelihood.

Disclosed herein is method for building patient trajectory models with consideration to the patients' outcome risks, allowing for prediction of different outcomes among individuals with similar trajectories. In embodiments, the computer-implemented method for predicting outcome risks described herein may be applied to a plurality of entities, such as medical patients, based on their trajectories. A dataset associated with the plurality of entities is obtained. The dataset may comprise medical data. An example dataset is depicted below, in Table 1. The depicted example dataset shows a sample ID (column 1), observed behavior/action data y at each time point (columns 2-4), time points at which sample data points y were taken (columns 5-7), risk factors (columns 8-10), and a predicted outcome (column 11).

TABLE 1

| 1 | 2 | 3 | 4 | 5 | 6 | 7 | 8 | 9 | 10 | 11 |
|---|---|---|---|---|---|---|---|---|----|----|
| ID | y1 | y2 | y3 ... | T1 | T2 | T3 ... | F1 | F2 | F3 ... | OUT-COME |
| 1 | 1 | 1 | 1 ... | 3 | 6 | 12 ... | 10 | 0 | 1 | 0 |
| 2 | 1 | 0 | 0 | 3 | 6 | 12 ... | 12 | 1 | 0 | 1 |
| ... | ... | ... | ... | 3 | 6 | 12 ... | ... | ... | ... | ... |

A set of parameters is determined from the dataset. The set of parameters may comprise a sample trajectory for each of the plurality of entities, a risk factor associated with one or more of the plurality of entities, and an outcome projected for each of the plurality of entities according to each entity's sample trajectory. The risk factor may comprise an adherence to, or deviation from, a medical protocol such as a medication regimen.

A posterior probability is calculated for each outcome using the set of parameters. The posterior probability expresses the likelihood that a given outcome will be true given current observations.

A maximum likelihood is determined for each outcome by applying gradient descent to a likelihood function ($\Pi_{i=1}^{N} f(y_i)$) using the posterior probability ($r_{ik}$). The likelihood function uses a mixture model of a trajectory model and an outcome model. The set of parameters is updated according to the maximum likelihood of each outcome. Possible updated parameters include group trajectory models, group outcome risks, and sample group memberships.

An updated trajectory model is built using the dataset, according to the updated set of parameters. The plurality of entities is grouped into subgroups according to the updated trajectory model. Each subgroup may contain one or more entities having a same or similar trajectory to each other. An alert associated with the entities in at least one of the subgroups may be generated according to a predicted outcome. For example, in some cases the alert may indicate that a medication, or other medical protocol, is likely to be ineffective and/or that the medication or protocol may be associated with one or more side effects. Such an alert may result from a trajectory indicating an increased risk and a predicted detrimental outcome associated with that increased risk. In other instances, the alert may indicate that a medication protocol is likely to be effective. Such an alert may indicate that a trajectory indicates decreased risk, and an associated desirable outcome, is predicted.

Referring now to FIG. 1A, an example graph 100 of group based trajectories is depicted. Graph 100 has an x-axis 102 and a y-axis 104. In example graph 100, x-axis 102 may represent the change in time and y-axis 104 may represent differences in behavior. Graph 100 displays group-based trajectories 106, 108, and 110. Each trajectory is a longitudinal sequence of behavioral measurements for an individual. Each individual may be any kind of entity, but some examples discussed herein are applications, devices, persons, etc. A behavior may be any repeated or continuous activity in which an individual may engage or perform (e.g., the latency in an application over time, or the frequency at which an application calls a diagnostic program). Examples of behavior related to medical practice may be a daily blood pressure measurement or record of a patient's adherence to a medication protocol. In some embodiments, groups may be of any size, provided all individuals exhibit behavior consistent with the trajectory pattern over time. Example graph 100 depicts trajectory 106 to be the trajectory of a first group (GROUP 1). Example graph 100 depicts trajectory 108 of a second group (GROUP 2). Example graph 100 depicts trajectory 110 of a third group (GROUP 3).

Figure 1B:
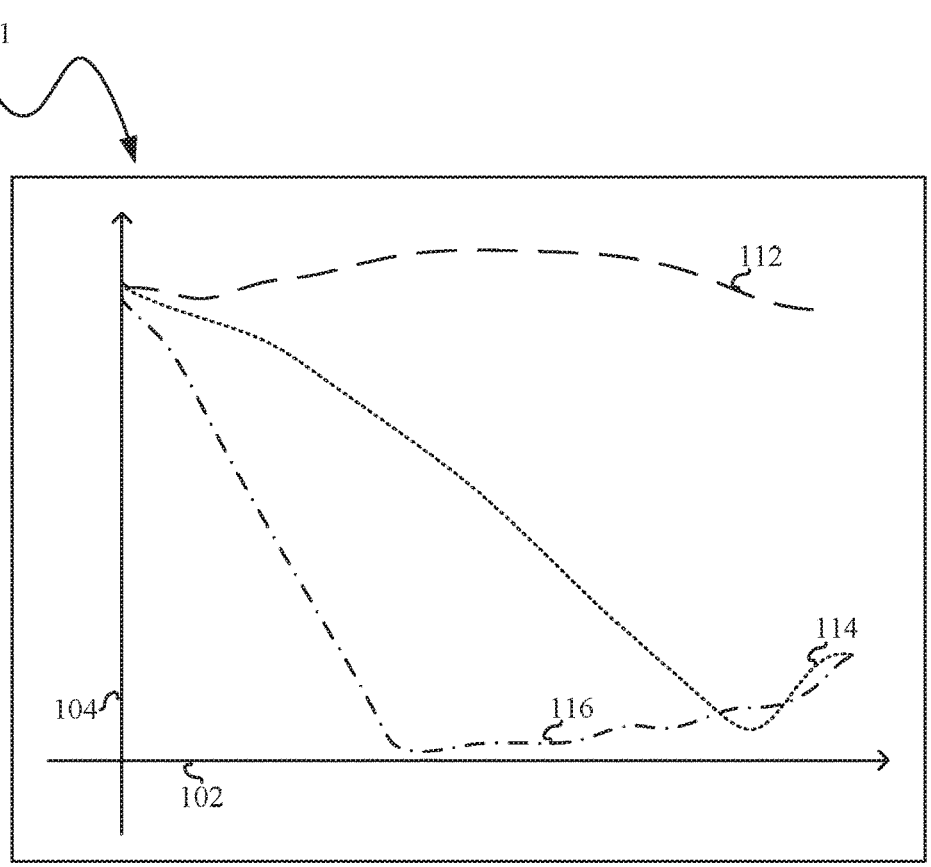
FIG. 1B depicts another example graph of group based trajectories.

Referring now to FIG. 1B, depicted is an example graph 101 of group based trajectories. The examples of graph 101, trajectories 112, 114, and 116, demonstrate the value of considering outcomes when establishing groups based on trajectories. Example graph 101, like graph 100 of FIG. 1A, has an x-axis 102, which may represent an environmental variable (e.g., time), and a y-axis 104, which may represent a behavioral variable (e.g., behavior measurements). Graph 101 may be an example of medical group-based trajectories. For example, the behavior measured on y-axis 104 may be adherence to a medication protocol. Adherence to a medication protocol may be measured as an amount of medication consumed by a patient (measured on the y-axis 104) in a given time period (measured on the x-axis 102).

In this example, trajectory 112 may represent a first group of patients having good adherence to a medication protocol (e.g., adherence to the prescription instructions for a hypertension drug). Trajectory 116 may represent a group having poor adherence to the medication protocol. Trajectory 114 may represent a group of patients who gradually drop-off the medication protocol. Each of trajectory patterns 112, 114, and 116 may have different associated disease risks. Each trajectory pattern may additionally have different risk prediction models, according to the variation in the behavior, e.g., the group represented by trajectory 112 may have a small risk associated with high blood pressure due to their good adherence to their hypertension medication, while the groups represented by trajectories 114 and 116 may have much higher risk associated with their blood pressures. The grouping of patients into the groups represented by the trajectories 112, 114, and 116 will affect the risk prediction performance of the model, e.g., without considering the outcome, members belonging to the group represented by trajectory 114 (declining adherence to the protocol) may be erroneously assigned to a group shared with individuals represented by trajectory 112 (good adherence to the protocol) due to their similar behaviors during early time periods. It may be possible to draw multiple trajectories according to a dataset. For example, FIG. 1A may be trajectories and groupings according to tracked blood pressures and FIG. 1B may be trajectories and groupings according to tracked medication consumption, wherein the dataset for each of FIG. 1A and FIG. 1B comprises the same plurality of individuals and each blood pressure data point from FIG. 1A may correspond to a medication data point in FIG. 1B. In instances wherein groupings according to different trajectory models coincide, additional information may be inferred. For example, trajectory 108 of FIG. 1A corresponds to "Group 2," if Group 2 is corresponds to trajectory 112 of FIG. 1B as well, it may be possible to infer a relationship regarding medication consumption (according to trajectory 112 of FIG. 1B) on blood pressure (according to trajectory 108 of FIG. 1A) or vice versa.

Figure 2:
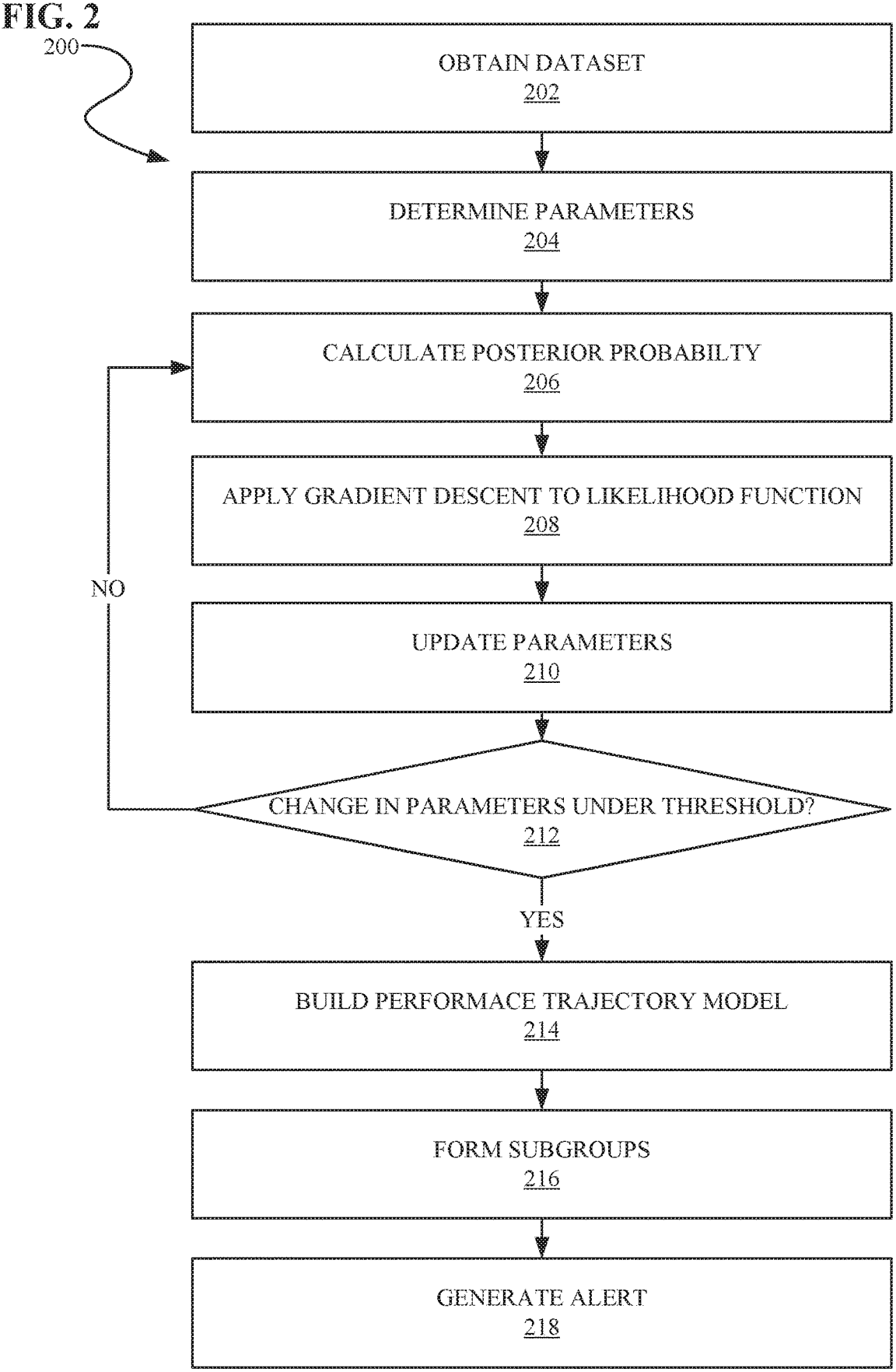
FIG. 2 depicts a flowchart of an example method for obtaining group-based trajectories with consideration to the outcomes, according to embodiments of the present disclosure.

FIG. 2 depicts a flowchart of an example method 200 for obtaining group-based trajectories with consideration to the outcomes, according to embodiments of the present disclosure. Method 200 may generally be carried out by one or more processors.

At operation 202, a dataset is obtained. The dataset may be formatted similar to Table 1 above. The dataset may generally contain a sequence of longitudinal measurements of a behavior and an associated trajectory (e.g., a sample trajectory), risk factors, and a project outcome. For example, a dataset for an application, or a group of applications, may include a series of longitudinal measurements of application performance, such as application response times, and an associated sample trajectory. The dataset may also contain risk factors, such as transaction load, and a projected outcome, such as reduced response time or application failure.

At operation 204, parameters are initialized. For example, if the dataset is not entered in a format that can be processed by the system, the dataset may be converted at this stage.

At operation 206, a posterior probability is calculated. The posterior probability may be calculated as $r_{ik}$ according the following equation:

$$r_{ik} = \frac{Pr(C_i = k) \; Pr(Y_i = y_i \mid C_i = k) \; Pr(O_i = o_i \mid C_i = k, X_i = x_i)}{\sum_{k=1}^{K} Pr(C_i = k) \; Pr(Y_i = y_i \mid C_i = k) Pr(O_i = o_i \mid C_i = k, X_i = x_i)}$$

where k is group membership, y is the sequence of longitudinal measurements of behavior, o is the outcome, and x is a series of risk factors.

At operation 208, a gradient descent is applied to a likelihood function to determine a maximum likelihood which is obtained from a mixture model combining the trajectory and the risk models based on the following:

$$L = \sum_{i=1}^{N} \sum_{k=1}^{K} r_{ik} \left( \log \theta_k + \sum_{y_{ij}=1} \log \left( \frac{\exp(\beta_{ok} + t_{ij}\beta_{1k} + t_{ij}^2 \beta_{2k} + \ldots)}{1 + \exp(\beta_{ok} + t_{ij}\beta_{1k} + t_{ij}^2 \beta_{2k} + \ldots)} \right) \right) +$$

$$\sum_{y_{ij}=0} \log \left( 1 - \frac{\exp(\beta_{ok} + t_{ij}\beta_{1k} + t_{ij}^2 \beta_{2k} + \ldots)}{1 + \exp(\beta_{ok} + t_{ij}\beta_{1k} + t_{ij}^2 \beta_{2k} + \ldots)} \right) +$$

$$O_i * \log \left( \frac{\exp(\alpha_{0k} + \alpha_{1k}x_1 + \alpha_{2k}x_2 + \ldots)}{1 + \exp(\alpha_{0k} + \alpha_{1k}x_1 + \alpha_{2k}x_2 + \ldots)} \right) +$$

$$(1 - O_i) * \log \left( 1 - \frac{\exp(\alpha_{0k} + \alpha_{1k}x_1 + \alpha_{2k}x_2 + \ldots)}{1 + \exp(\alpha_{0k} + \alpha_{1k}x_1 + \alpha_{2k}x_2 + \ldots)} \right) - \log(r_{ik})$$

Based on the output of the likelihood function, parameters are updated, as at operation 210.

At decision block 212, the change in parameters between the updated parameters (from operation 210) and the parameters prior to the update (from operation 204) is assessed to determine whether the change falls under a predetermined threshold. If the change in parameters is determined not fall under the predetermined threshold, the process may return to operation 206 and calculate a new posterior probability using the updated parameters. The steps of operation 204, determining parameters, operation 206, calculating a posterior probability, operation 208, applying a gradient descent to a likelihood function, and operation 210, updating the parameters, may be performed iteratively until the change in parameters is determined to fall under a predetermined threshold, at decision block 212.

If, at decision block 212, the change in parameters is determined to fall under the predetermined threshold, a performance trajectory model is built, as at operation 214. The change in parameters may be calculated as the sum of the squared change in each parameter according to:

$$(\Delta p_1)^2 + (\Delta p_2)^2 + \ldots (\Delta p_n)^2$$

where p is the parameter value. The predetermined threshold may be a part of the settings of a system executing the method, or set at the start of the process. The purpose of the predetermined threshold may be to determine when the change in parameters have stabilized.

At operation 216, subgroups are formed. The subgroups are organized according to the performance trajectory model. As trajectories may have shifted from the sample trajectory to the performance trajectory model, the final group or subgroup an entity is assigned to may differ from its initial grouping, due to accounting for projected outcome.

At operation 218, an alert is generated. Alerts generated by method 200 may be merely informative or may trigger a system response, e.g., automatically redistributing files or initiating a diagnostic program.

Figure 3A:
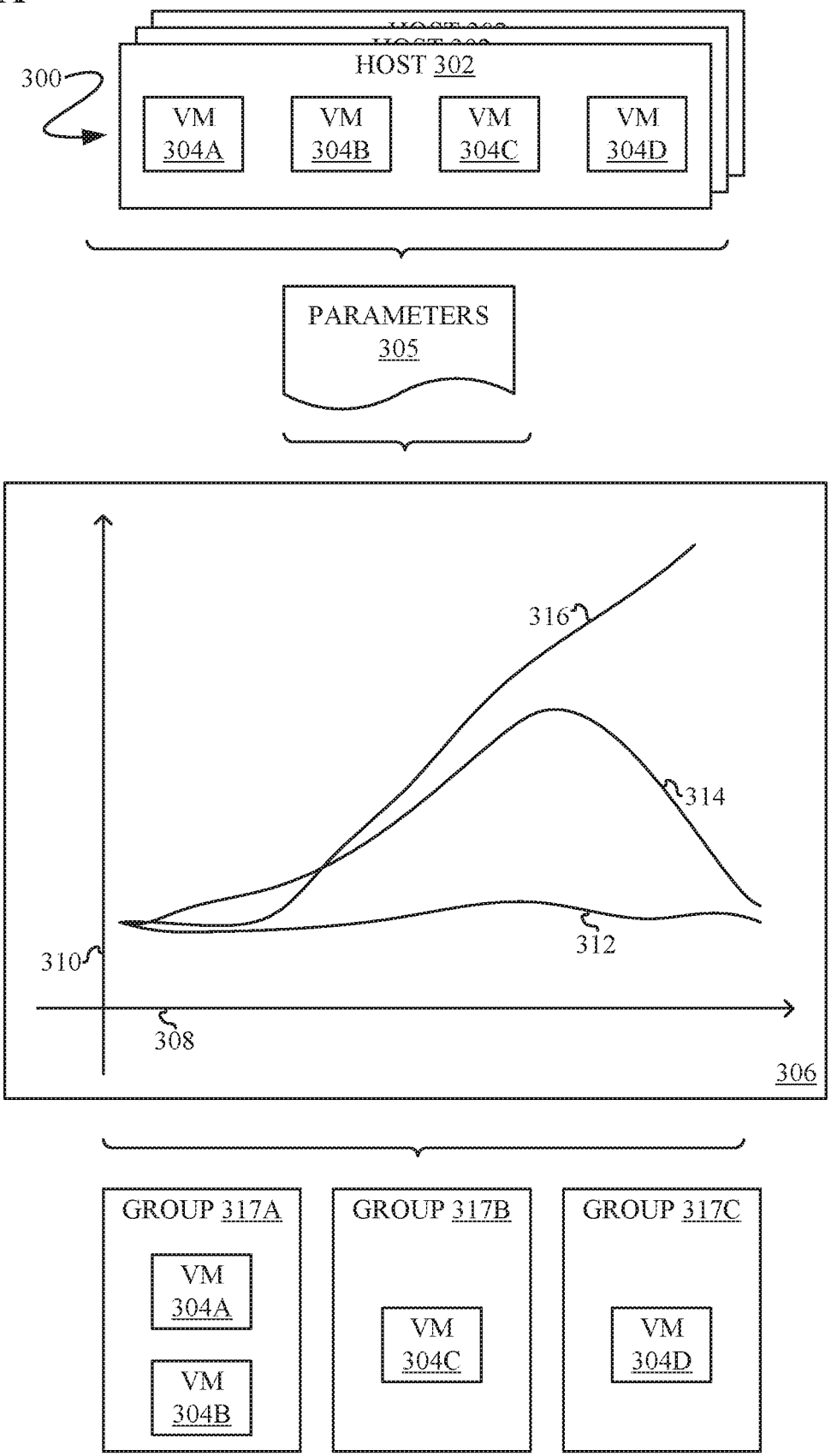
FIG. 3A depicts an example of generating a trajectory-grouping model, according to embodiments of the present disclosure.

Referring now to FIG. 3A, depicted is an example of generating an outcome-based trajectory-grouping model, according to embodiments of the present disclosure. In the example of FIG. 3, the method, e.g., method 200 of FIG. 2, is applied to a virtual system 300. The virtual system 300 comprises a number of hosts 302, each hosting a number of virtual machines 304A, 304B, 304C, 304D (collectively virtual machines 304).

Each of virtual machines 304 has a one or more measureable behaviors or actions, such as I/O latency (explored in this example), response time, processing time, utilization of resources, availability of the system or an application, data compression/decompression speeds, data transmission time, etc. The actions or behaviors of the virtual machines 304 may be tracked over time to develop or obtain a dataset which is used to develop a set of parameters 305. In embodiments, parameters 305 may be a table similar to Table 1 above. Parameters 305 contain the recorded actions or behaviors of the virtual machines 304, along with the time points of the recorded actions or behaviors and the outcomes. Parameters 305 may additionally contain risk factors, or characteristics associated with a given outcome, associated with virtual machines 304. In this example, looking at I/O latency, risk factors may include storage availability, the presence of malware, whether multiple applications are running on the virtual machine, etc.

Parameters 305 may be used to develop a trajectory model 306, such as by using the method 200 (from FIG. 2) described above. Using the described method, a posterior probability is calculated from parameters 305 and used to determine maximum likelihood from parameters 305. The maximum likelihood is determined using the likelihood function with consideration of the outcomes:

$$L = \Sigma_{i=1}^{N} \log(\Sigma_{k=1}^{K} Pr(C_i=k) Pr(Y_i=y_i \mid C_i=k) Pr(O_i=o_i \mid C_i=k, X_i=x_i))$$

using to posterior probability and gradient decent. Taking steps proportional to the negative of the gradient (or approximate gradient) of a sample trajectory, the local minimum of the function (associated with the maximum likelihood of a given outcome) is approached.

In embodiments the parameters 305 may adjusted according to the maximum likelihood. For example, parameters 305 may include a hypothetical outcome, and the outcome determined from the maximum likelihood may differ from the hypothetical outcome of parameters 305. If the difference between the outcome determined from the maximum likelihood and the hypothetical outcome of parameters 305 exceeds a predetermined threshold, then parameters 305 may be updated accordingly and a trajectory model 306 produced from the updated parameters.

For example, the response times of virtual machines 304 may be a tracked parameter as part of parameters 305. As the virtual machine's function, the likelihood of an unacceptable response times (e.g., longer than 1 second) is updated according to the calculated maximum likelihood. For each virtual machine 304, a maximum likelihood (e.g., 50% chance of unacceptable response time) is calculated based on tracked response times. This is used to update the response time parameter of parameters 305.

The trajectory model 306 shows "instances of high latency" on y-axis 310 and "time" on x-axis 308. Graph 306 depicts three different trajectories 312, 314, 316, according to how many instances of high latency (e.g., latency exceeding a predetermined threshold) occur in a period of time (e.g., an hour) tracked over time (hour-to-hour). Trajectory 312 can be seen to have a stable, relatively low number of instances of high latency. Trajectory 316 can be seen to have a steadily increasing number of instances of high latency. Trajectory 314 can be seen to be seen to initially progress in a similar pattern to trajectory 316, before changing course and ending with an outcome similar to trajectory 312.

Virtual machines 304 may be grouped into groups 317A, 317B, 317C (collectively groups 317) according to their individual trajectory following one of trajectories 312, 314, 316 of trajectory model 306. For example, if both of virtual machines 304A and 304B are found to follow trajectory 316 then virtual machines 304A and 304B may be grouped together in group 317A. Virtual machine 304C may be found to follow trajectory 314 and be assigned to group 317B, and virtual machine 304D may be found to have a low, stable number of high latency instances, thus following trajectory 312, and be assigned to group 317C. As discussed above, parameters 305 may contain a number of risk factors associated with each virtual machine 304, which may then in turn be associated with a given trajectory 312, 314, 316 and outcome. Trajectories, outcomes, and risk factors may in turn be associated with a given group 317 and the virtual machines 304 found to fit with that group. In this way, an outcome-based trajectory group model may be built, wherein entities (virtual machines 304 in this example) are analyzed and their trajectories tracked, allowing the units to be grouped according to similar risk factors and likely outcomes for the grouped machines predicted according to the model 306. Further, accounting for the outcomes when assembling the trajectory model 306 provides for more accurate grouping of virtual machines 304 into groups 317. In this example, trajectories 314 and 316 overlap for much of the time tracked data, only diverging in the latter part of the x-axis 308. By accounting for outcomes when assembling the trajectory model 306, conflation of the two groups, trajectories 314 and 316 in this example, may be avoided.

Figure 3B:
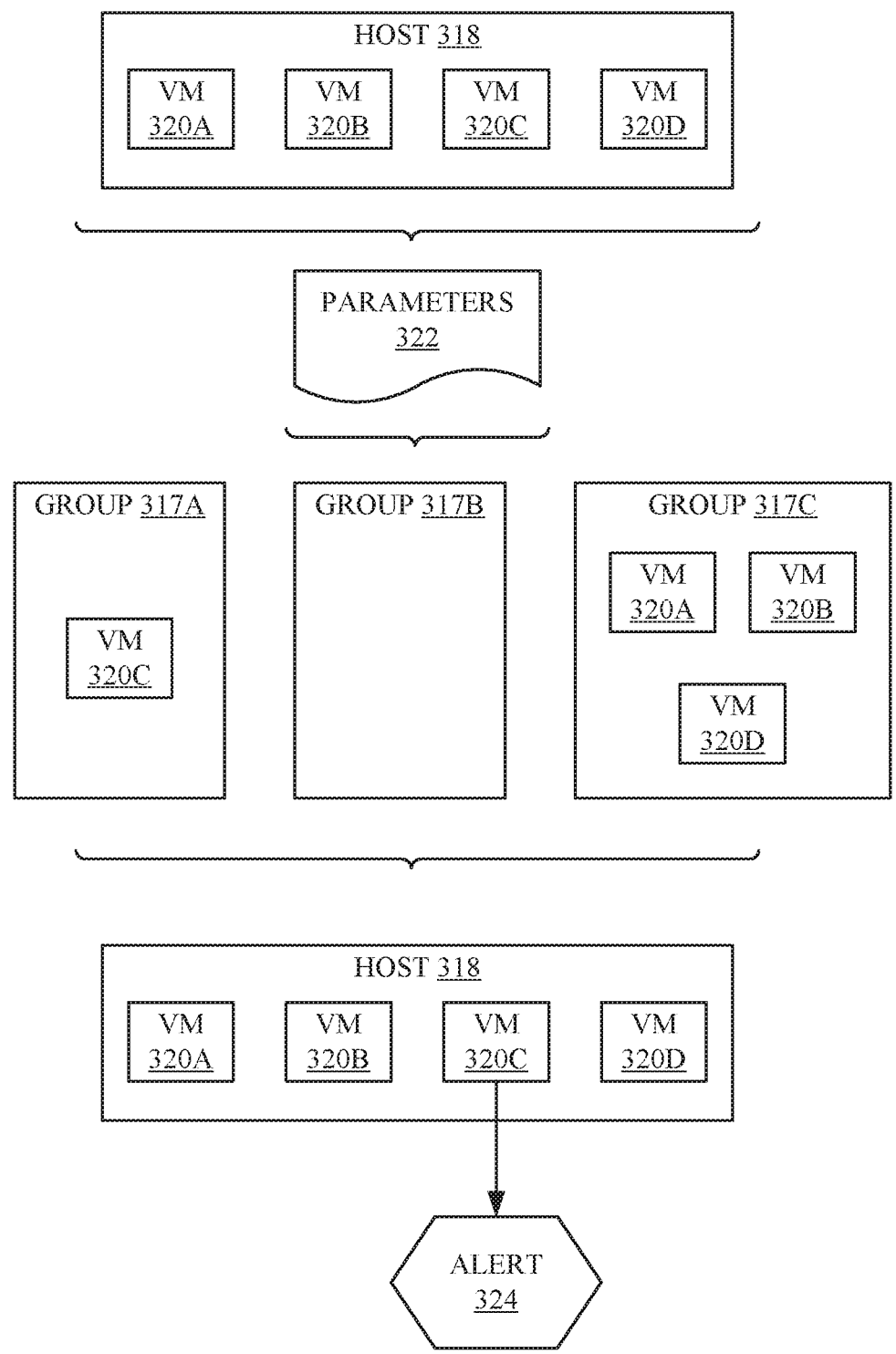
FIG. 3B depicts an example of applying a trajectory-grouping model, according to embodiments of the present disclosure.

Referring now to FIG. 3B, depicted is an example of applying a trajectory-grouping model (such as the trajectory grouping model 306 as discussed in relation to FIG. 3A), according to embodiments of the present disclosure. In applying the trajectory grouping model, following from the example above, a new host 318 with a new assembly of virtual machines 320A, 320B, 320C, 320D (collectively virtual machines 320) may be analyzed to acquire new parameters 322. In embodiments, new parameters 322 may represent a more limited data set than parameters 305 of FIG. 3A, used to develop the trajectory grouping model 306. For example, parameters 322 may contain behavioral data for a more limited set of time points, and relatedly, may not contain outcome data. Parameters 322 may contain risk factors associated with each virtual machine 320.

From new parameters 322, each of virtual machines 320 may be compared with the developed trajectory model 306 (from FIG. 3A) and each of virtual machines 320 assigned to a group 317 according to the comparison of parameters 322 against trajectory model 306. In this example, virtual machine 320C is found to fit with trajectory 316, and is accordingly assigned to group 317A. Each of virtual machines 320A, 320B, and 320D is found to fit with trajectory 312, and are accordingly assigned to group 317C. Virtual machines 320 may be found to fit with a particular trajectory based on measured behavioral data and individual risk factors.

Virtual machines 320 may be sorted into groups 317 according to their fit with a particular trajectory of trajectory model 306 (from FIG. 3A). For instance, virtual machines 320A, 320B, and 320D may be found, according to parameters 322, to have a stable number of relatively low high latency instances and therefore to fit with group 317C according to the trajectory 312 (from FIG. 3A). As the outcome of trajectory 312 was accounted for when creating trajectory model 306 (according to method 200 of FIG. 2), the outcome for virtual machines 320A, 320B, and 320D can be predicted according to the model 306. According to the trajectory 312, associated with the group 317C, virtual machines 320A, 320B, and 32D may be predicted to continue in their stable pattern.

According to parameters 322, virtual machine 320C is assigned to group 317A, associated with trajectory 316 (from FIG. 3A, as discussed above) showing an increasing trend in instances of high latency. As trajectory 316, and thus group 317A, is accordingly associated with a potentially negative outcome, an alert 324 may be generated for virtual machine 320C, which may be predicted to have continuing increases in latency, according to the trajectory 316 of the trajectory model 306.

Referring now to FIG. 4, shown is a high-level block diagram of an example computer system (i.e., computer) 400 that may be used in implementing one or more of the methods or modules, and any related functions or operations, described herein (e.g., using one or more processor circuits or computer processors of the computer), in accordance with embodiments of the present disclosure. In some embodiments, the major components of the computer system 400 may comprise one or more CPUs 402, a memory subsystem 404, a terminal interface 412, an I/O (Input/Output) device interface 414, a storage interface 416, and a network interface 418, all of which may be communicatively coupled, directly or indirectly, for inter-component communication via a memory bus 403, an I/O bus 408, and an I/O bus interface unit 410.

The computer system 400 may contain one or more general-purpose programmable central processing units (CPUs) 402A, 402B, 402C, and 402D, herein generically referred to as the CPU 402. In some embodiments, the computer system 400 may contain multiple processors typical of a relatively large system; however, in other embodiments the computer system 400 may alternatively be a single CPU system. Each CPU 402 may execute instructions stored in the memory subsystem 404 and may comprise one or more levels of on-board cache.

In some embodiments, the memory subsystem 404 may comprise a random-access semiconductor memory, storage device, or storage medium (either volatile or non-volatile) for storing data and programs. In some embodiments, the memory subsystem 404 may represent the entire virtual memory of the computer system 400, and may also include the virtual memory of other computer systems coupled to the computer system 400 or connected via a network. The memory subsystem 404 may be conceptually a single monolithic entity, but, in some embodiments, the memory subsystem 404 may be a more complex arrangement, such as a hierarchy of caches and other memory devices. For example, memory may exist in multiple levels of caches, and these caches may be further divided by function, so that one cache holds instructions while another holds non-instruction data, which is used by the processor or processors. Memory may be further distributed and associated with different CPUs or sets of CPUs, as is known in any of various so-called non-uniform memory access (NUMA) computer architectures. In some embodiments, the main memory or memory subsystem 404 may contain elements for control and flow of memory used by the CPU 402. This may include a memory controller 405.

Although the memory bus 403 is shown in FIG. 4 as a single bus structure providing a direct communication path among the CPUs 402, the memory subsystem 404, and the I/O bus interface 410, the memory bus 403 may, in some embodiments, comprise multiple different buses or communication paths, which may be arranged in any of various forms, such as point-to-point links in hierarchical, star or web configurations, multiple hierarchical buses, parallel and redundant paths, or any other appropriate type of configuration. Furthermore, while the I/O bus interface 410 and the I/O bus 408 are shown as single respective units, the computer system 400 may, in some embodiments, contain multiple I/O bus interface units 410, multiple I/O buses 408, or both. Further, while multiple I/O interface units are shown, which separate the I/O bus 408 from various communications paths running to the various I/O devices, in other embodiments some or all of the I/O devices may be connected directly to one or more system I/O buses.

In some embodiments, the computer system 400 may be a multi-user mainframe computer system, a single-user system, or a server computer or similar device that has little or no direct user interface, but receives requests from other computer systems (clients). Further, in some embodiments, the computer system 400 may be implemented as a desktop computer, portable computer, laptop or notebook computer, tablet computer, pocket computer, telephone, smart phone, mobile device, or any other appropriate type of electronic device.

It is noted that FIG. 4 is intended to depict the representative major components of an exemplary computer system 400. In some embodiments, however, individual components may have greater or lesser complexity than as represented in FIG. 4, components other than or in addition to those shown in FIG. 4 may be present, and the number, type, and configuration of such components may vary.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to explain the principles of the embodiments, the practical application or technical improvement over technologies found in the marketplace, or to enable others of ordinary skill in the art to understand the embodiments disclosed herein.

What is claimed is:

1. A computer system for predicting outcome risk associated with a trajectory comprising:
   a memory;
   a processor in communication with the memory, wherein the processor is configured to perform a method, the method comprising:
      obtaining a dataset associated with computing performance of a plurality of servers;
      determining, from the dataset, a set of parameters comprising a sample performance trajectory for each of the plurality of servers, a risk factor associated with one or more of the plurality of servers, and a performance outcome projected for each of the plurality of servers according to each server's sample performance trajectory;
      determining a maximum likelihood of each performance outcome using a likelihood function, the likelihood function being a mixture model of a trajectory model and an outcome model;
      updating the set of parameters according to the maximum likelihood of each performance outcome;
      building a performance trajectory model, using the dataset, according to the updated set of parameters;
      grouping the plurality of servers into subgroups according to the performance trajectory model, each subgroup containing one or more servers, and each of the one or more servers in a given subgroup having a same or similar trajectory to each other;
      generating at least one alert associated with servers in at least one subgroup, wherein the alert indicates that the servers in the at least one subgroup exceed a predetermined risk level for server failure;
      transmitting the at least one alert to the servers in the at least one subgroup; and
      increasing, by the servers in the at least one subgroup, power to one or more cooling systems associated with one or more servers in the at least one subgroup.

2. The computer system of claim 1, wherein the maximum likelihood is calculated by applying gradient descent to the likelihood function.

3. The computer system of claim 2, wherein a posterior probability is used to apply gradient descent to the likelihood function.

4. The computer system of claim 3, wherein the posterior probability is calculated, using the set of parameters, for each outcome.

5. The computer system of claim 4, wherein the method steps of calculating, using the set of parameters, a posterior probability according to the dataset; applying gradient descent to a likelihood function, using the posterior probability, to determine a maximum likelihood; and obtaining updated parameters according to the maximum likelihood are performed iteratively until a difference between a most recent set parameters and an immediately preceding set of parameters reaches a predetermined threshold.

6. A computer-implemented method for predicting outcome risks for a plurality of servers based on trajectories, the method comprising:
   obtaining a dataset associated with the plurality of servers;
   determining, from the dataset, a set of parameters comprising a sample trajectory for each of the plurality of servers, a risk factor associated with one or more of the plurality of servers, and an outcome projected for each of the plurality of servers according to each server's sample trajectory;
   calculating a maximum likelihood of each outcome using a likelihood function, the likelihood function being a mixture model of a trajectory model and an outcome model;
   updating the set of parameters according to the maximum likelihood of each outcome;
   building an updated trajectory model, using the dataset, according to the updated set of parameters;
   grouping the plurality of servers into subgroups according to the updated trajectory model, each subgroup containing one or more servers, and each of the one or more servers in a given subgroup having a same or similar trajectory to each other;
   generating at least one alert associated with servers in at least one subgroup, wherein the alert indicates that the servers in the at least one subgroup exceed a predetermined risk level for server failure;
   transmitting the at least one alert to the servers in the at least one subgroup; and
   increasing, by the servers in the at least one subgroup, power to one or more cooling systems associated with one or more servers in the at least one subgroup.

7. The method of claim 6, wherein the maximum likelihood is calculated by applying gradient descent to the likelihood function.

8. The method of claim 7, wherein a posterior probability is used to apply gradient descent to the likelihood function.

9. The method of claim 8, wherein the posterior probability is calculated, using the set of parameters, for each outcome.

10. The method of claim 6, wherein the steps of calculating a maximum likelihood and obtaining updated parameters according to the maximum likelihood are performed iteratively until a difference between a most recent set parameters and an immediately preceding set of parameters reaches a predetermined threshold.

11. A computer program product for predicting outcome risks for a plurality of servers based on trajectories, the computer program product comprising a computer readable storage medium having program instructions embodied therewith, wherein the computer readable storage medium is not a transitory signal per se, the program instructions executable by a processor to perform a method comprising:

obtaining a dataset associated with the plurality of servers;

determining, from the dataset, a set of parameters comprising a sample trajectory for each of the plurality of servers, a risk factor associated with one or more of the plurality of servers, and an outcome projected for each of the plurality of servers according to each server's sample trajectory;

calculating, using the set of parameters, a posterior probability for each outcome;

applying gradient descent to a likelihood function, using the posterior probability, to determine a maximum likelihood of each outcome, the likelihood function being a mixture model of a trajectory model and an outcome model;

updating the set of parameters according to the maximum likelihood of each outcome;

building an updated trajectory model, using the dataset, according to the updated set of parameters;

grouping the plurality of servers into subgroups according to the updated trajectory model, each subgroup containing one or more servers, and each of the one or more servers in a given subgroup having a same or similar trajectory to each other;

generating at least one alert associated with servers in at least one subgroup, wherein the alert indicates that the servers in the at least one subgroup exceed a predetermined risk level for server failure;

transmitting the at least one alert to the servers in the at least one subgroup; and increasing, by the servers in the at least one subgroup, power to one or more cooling systems associated with one or more servers in the at least one subgroup.

12. The computer program product of claim 11, wherein the steps of calculating a maximum likelihood and obtaining updated parameters according to the maximum likelihood are performed iteratively until a difference between a most recent set parameters and an immediately preceding set of parameters reaches a predetermined threshold.

* * * * *